United States Patent
Weinberg et al.

(10) Patent No.: US 11,686,793 B2
(45) Date of Patent: Jun. 27, 2023

(54) UNILATERAL MAGNETIC RESONANCE IMAGING SYSTEM WITH APERTURE FOR INTERVENTIONS AND METHODOLOGIES FOR OPERATING SAME

(71) Applicant: Weinberg Medical Physics, Inc., North Bethesda, MD (US)

(72) Inventors: Irving N. Weinberg, North Bethesda, MD (US); Aleksandar Nelson Nacev, San Francisco, CA (US); Ryan Hilaman, Oakland, CA (US); Amit Vohra, Rocklin, CA (US)

(73) Assignee: WEINBERG MEDICAL PHYSICS INC

( * ) Notice: Subject to any disclaimer, the term of this patent is extended or adjusted under 35 U.S.C. 154(b) by 342 days.

(21) Appl. No.: 16/003,585

(22) Filed: Jun. 8, 2018

(65) Prior Publication Data

US 2018/0356480 A1    Dec. 13, 2018

Related U.S. Application Data

(60) Provisional application No. 62/516,698, filed on Jun. 8, 2017.

(51) Int. Cl.
*G01R 33/38* (2006.01)
*G01R 33/34* (2006.01)
*A61B 5/055* (2006.01)
*G01R 33/3415* (2006.01)
*A61B 5/00* (2006.01)
*G01R 33/383* (2006.01)

(52) U.S. Cl.
CPC .......... *G01R 33/3808* (2013.01); *A61B 5/055* (2013.01); *A61B 5/702* (2013.01); *G01R 33/3415* (2013.01); *A61B 5/4571* (2013.01); *G01R 33/383* (2013.01)

(58) Field of Classification Search
CPC .............. G01R 33/3808; G01R 33/381; G01R 33/383; G01R 33/3415
See application file for complete search history.

(56) References Cited

U.S. PATENT DOCUMENTS

| | | | |
|---|---|---|---|
| 4,721,914 A | 1/1988 | Fukushima et al. | |
| 5,382,904 A * | 1/1995 | Pissanetzky | G01R 33/3815 324/319 |
| 6,262,576 B1 | 7/2001 | Petropoulos | |
| 6,489,872 B1 | 12/2002 | Fukushima et al. | |
| 7,271,589 B2 * | 9/2007 | Melzi | G01R 33/341 324/318 |
| 8,154,286 B2 | 4/2012 | Weinberg | |
| 2008/0306377 A1 | 12/2008 | Piron et al. | |
| 2009/0082690 A1 | 3/2009 | Phillips et al. | |

(Continued)

FOREIGN PATENT DOCUMENTS

JP    2002325743 A    11/2002

OTHER PUBLICATIONS

International Search Report and Written Opinion for International Patent Application No. PCT/US2018/36686; dated Sep. 6, 2018.

*Primary Examiner* — Reena Aurora
(74) *Attorney, Agent, or Firm* — Barnes & Thornburg LLP

(57) ABSTRACT

An imaging apparatus and methodologies image a subject using an MRI, wherein the imaging apparatus contains only a single sided device for the purposes of imaging structures in the subject.

14 Claims, 2 Drawing Sheets

(56) References Cited

U.S. PATENT DOCUMENTS

| | | |
|---|---|---|
| 2009/0315560 A1 | 12/2009 | Weinberg |
| 2012/0262261 A1 | 10/2012 | Sarai |
| 2012/0265050 A1* | 10/2012 | Wang ............... A61B 5/055 |
| | | 600/411 |
| 2015/0112187 A1* | 4/2015 | Petropoulos ......... A61B 6/0421 |
| | | 600/422 |
| 2017/0139024 A1 | 5/2017 | Nacev |
| 2017/0227617 A1 | 8/2017 | Weinberg |
| 2020/0309878 A1* | 10/2020 | Popescu ............ G01R 33/3808 |

* cited by examiner

UNILATERAL MAGNETIC RESONANCE IMAGING SYSTEM WITH APERTURE FOR INTERVENTIONS AND METHODOLOGIES FOR OPERATING SAME

CROSS REFERENCE AND PRIORITY CLAIM

This patent application claims priority to U.S. Provisional Application Provisional Patent Application No. Patent Application Ser. No. 62/516,698, entitled "UNILATERAL MAGNETIC RESONANCE IMAGING SYSTEM WITH APERTURE FOR INTERVENTIONS," filed Jun. 8, 2017, the disclosure of which being incorporated herein by reference in its entirety.

FIELD OF USE

Disclosed embodiments provide a method and apparatus for clinical imaging or therapy of living beings or examination of inanimate objects.

BACKGROUND

In conventional Magnetic Resonance Imaging (MRI) scanners, the magnetic field used to generate the image is created by a device that is located around the subject. For the purposes of this specification, the term "subject" is understood to be a human or other animal with or without illness. For example, a super conducting clinical MRI usually consists of a superconducting solenoid whose bore becomes the imaging volume. The subject, or patient, is guided into the bore where all imaging is conducted. However, due to the limited size of the bore, these MRI systems restrict patient mobility and can inhibit the permissible patient body sizes that can be imaged.

To enable greater patient mobility and flexibility, open MRI systems have been developed. These typically consist of bi-planar magnetic field generating components which create a magnetic field within the gap of the two planes. The patient is again imaged within the gap. Typically, the gap distance in these systems is larger than the solenoid configuration of superconducting magnets, but the patient is still enclosed by the MR system.

SUMMARY

Disclosed embodiments provide a new imaging apparatus and methodologies to image a subject using an MRI, wherein the imaging apparatus contains only a single sided device for the purposes of imaging structures in the subject. For the purposes of this specification, the terms "single sided device" and "single-sided device" are understood to mean a device placed less than 360 degrees around a subject in order to operate. For example, a conventional cylindrical MRI bore would not be considered a single-sided device.

In accordance with at least one embodiment, such an apparatus and corresponding methodologies may be used to image, for example, the pelvic region of a subject.

In accordance with disclosed embodiments, due to the non-encompassing geometry of the innovative imaging apparatus, the subject's mobility is less restricted compared to conventional MRI scanners.

In accordance with disclosed embodiments, a single-sided MRI system is provided that includes access apertures through which interventions on the subject can be made. For the purposes of this specification, the term "intervention" is understood to be a biopsy or method of treatment involving physical access to a part of the subject.

BRIEF DESCRIPTION OF THE FIGURES

The detailed description particularly refers to the accompanying figures in which.

DETAILED DESCRIPTION

Conventional single-sided MRI systems do not provide access apertures through which interventions could be made. Examples of such conventional systems include U.S. Pat. No. 4,721,914 to Eiichi Fukushima, entitled "Apparatus for Unilateral Generation of a Homogeneous Magnetic Field" (incorporated by reference in its entirety), and U.S. Pat. No. 6,489,872 by the same inventor, entitled "Unilateral Magnet Having a Remote Uniform Field Region for Nuclear Magnetic Resonance" (incorporated by reference in its entirety).

Figure 1:
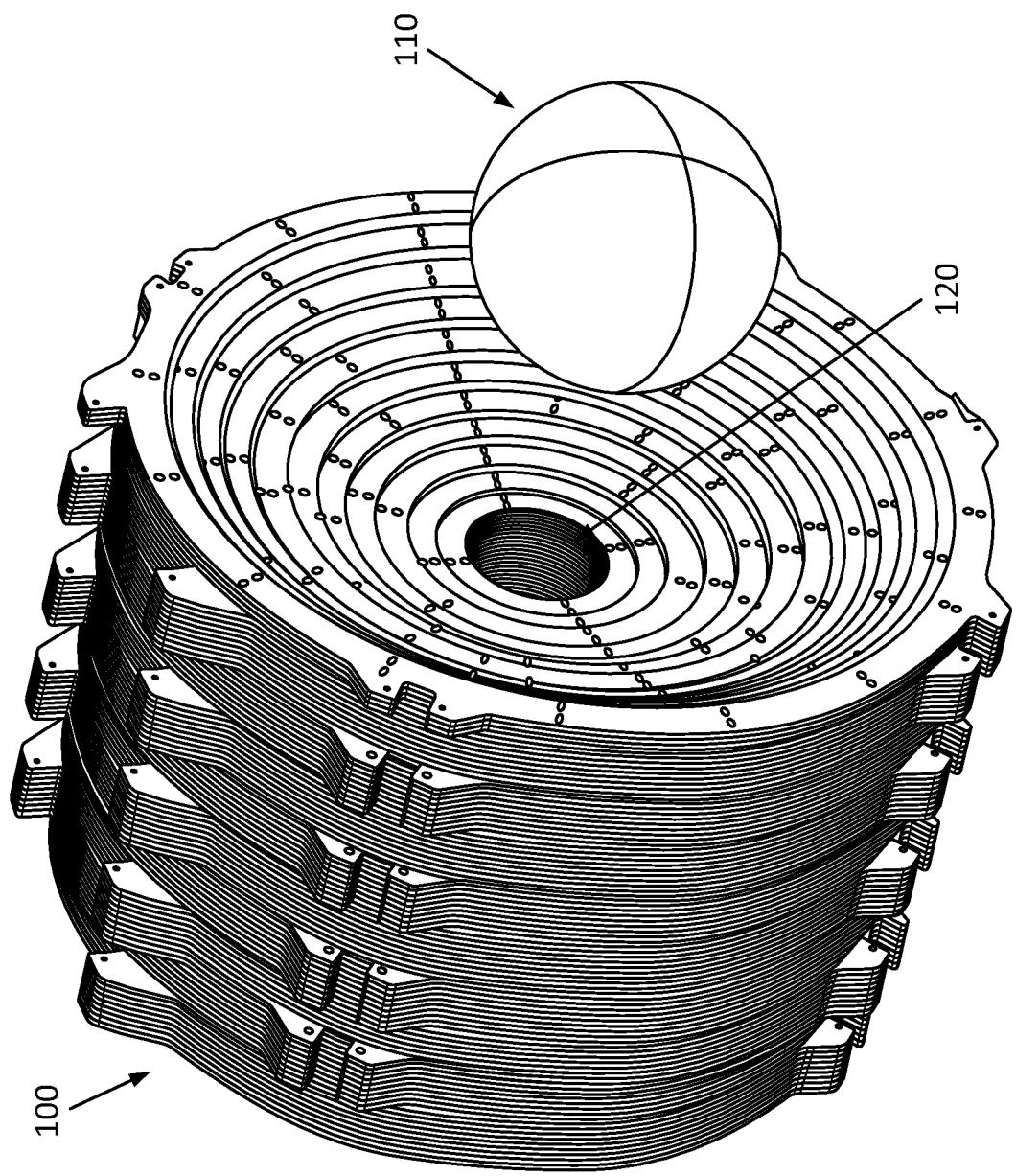
FIG. 1 shows an embodiment of the disclosed invention, in which a magnet field generating apparatus is placed in proximity to a region of interest.

To the contrary, in accordance with disclosed embodiments, a single-sided MRI system is provided that includes access apertures through which interventions on the subject can be made. FIG. 1 illustrates an embodiment of the invention wherein a magnet field generating apparatus 100 is placed in proximity to a region of interest 110. As shown in FIG. 1, there exists an access aperture 120 that is perpendicular to the face of the magnet assembly 100 that is near to the region of interest 110.

Disclosed embodiments utilize a magnetic field generating apparatus 100 and a radio frequency generating and recording device 130 positioned on one face of the device. The magnetic field generating apparatus 100 may be positioned near to only a single face of the region of interest 110. The geometrical configuration of the apparatus 100 may include one or more apertures or access holes 120. This configuration enables intervention with the subject, e.g., a human or animal patient/subject can be easily repositioned. Additionally, the one or more apertures or access holes 120 enable increased access to one or more structures in the subject to be imaged.

Figure 2:
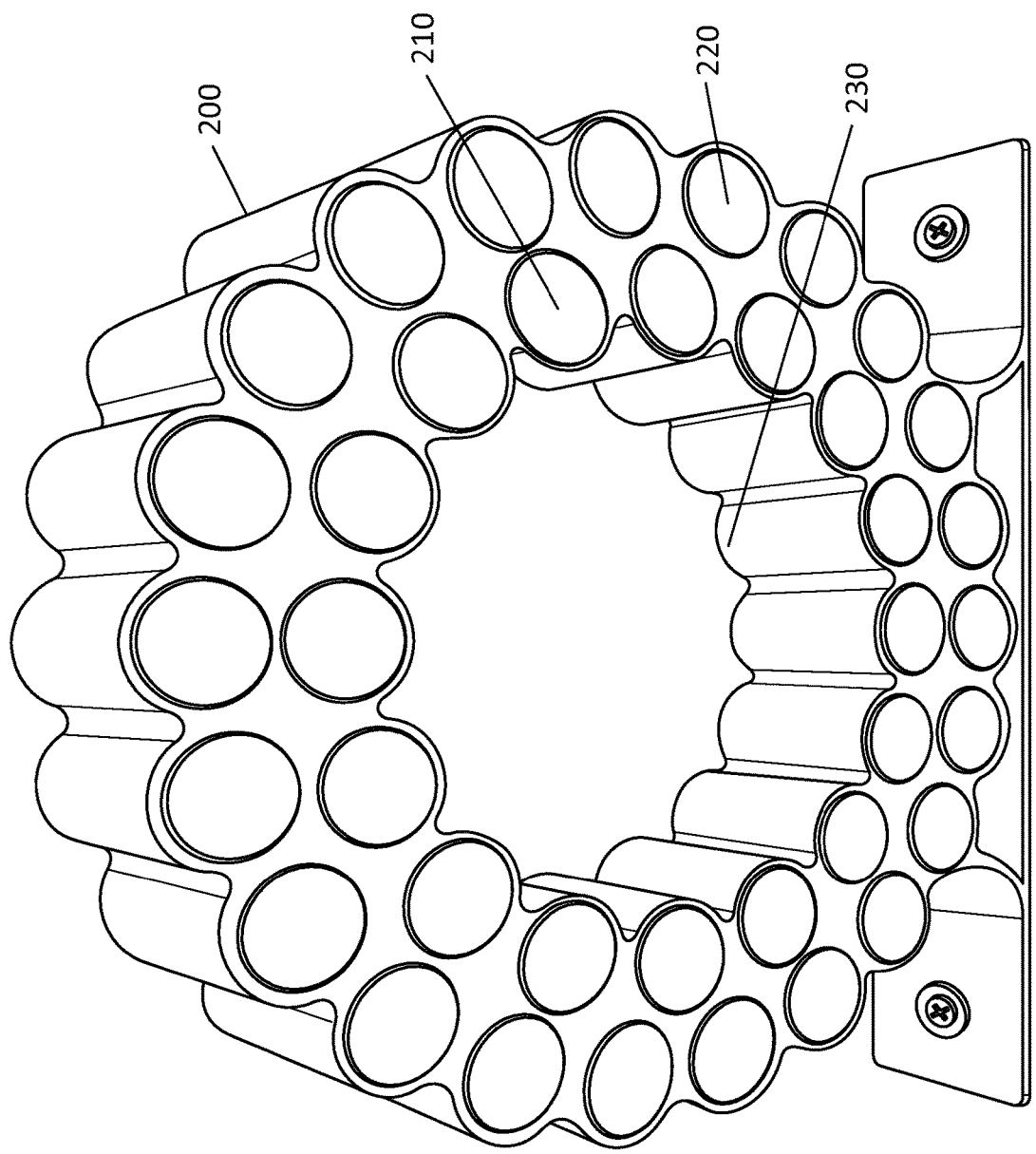
FIG. 2 shows an example of a composition of one layer of a magnetic field generating apparatus composed of layers of magnets in accordance with a disclosed embodiment.

The magnetic field generating apparatus 100 may be composed of layers of magnets, one layer of which being composed as illustrated in FIG. 2. As shown in FIG. 2, the layer 200 contains magnets 210 and 220, which are oriented in directions so as to provide magnetic fields opposing the magnetic field provided by a magnet in the same or other layers. For example, as shown in FIG. 2, magnet 210 may be oriented in a position so as to provide a magnetic field opposing the magnetic field produced by magnet 220 in the same layer. The aperture is illustrated as aperture 230 in FIG. 2.

In accordance with disclosed embodiments, the magnetic field generating device 100 may include one or more arrays of magnetic components, examples of which being 210 and 220 in one or more layers (an example of which being 200).

These layers may generate a desired magnetic profile that is either uniform in magnetic field strength to a certain degree of homogeneity, or with a built in magnetic field gradient that varies linearly in space, or with another well characterized magnetic field profile shape suitable for imaging over a region 110. In accordance with at least one embodiment, the magnetic profile in region 110 may be uniform. Alternatively, in accordance with at least one embodiment, the magnetic profile in region 110 may not be uniform, in which case an appropriate algorithm for reconstruction may be used to generate an image. An example of such an algorithm was provided by Dominic Holland et al. published in the journal Neuroimage volume 50, pages 175-183 in 2010, entitled "Efficient correction of inhomogeneous static magnetic field-induced distortion in Echo Planar Imaging" (incorporated by reference in its entirety). Other correction methods may be applied, for example using maximum likelihood reconstructions. Likewise, generation of the magnetic profile may be performed in accordance with patented innovations for imaging of living tissue.

More specifically, the imaging system 130 may include electrical coils and/or electro-permanent magnets, in which the electro-permanent magnets that are magnetized by a transient current flowing through electrical coils and stay activated until the magnetization is removed by other transient currents flowing through electrical coils. Radiofrequency, gradient, pre-polarizing and/or shimming coils that may be needed to form an image may also be included.

Optionally, ultra-fast and high-magnitude gradient pulses as described by Irving Weinberg in U.S. Pat. No. 8,154,286, entitled "APPARATUS AND METHOD FOR DECREASING BIO-EFFECTS OF MAGNETIC FIELDS," and related patents and patent applications (related by priority claims), all being incorporated by reference, may be used to collect many sets of data points in order to achieve high spatial resolution and signal-to-noise ratio, without causing uncomfortable nerve stimulation. Such high magnetic gradient field magnitude may be 400 mT or higher, with rise-times of 10 microseconds or less. The gradient pulses may be so rapid as to permit acquisition in a very short time, for example 10 seconds or less, so that there is little motion of the breast during acquisition, thereby reducing resolution loss from "motion-unsharpness."

Optionally, in accordance with at least one embodiment, pre-polarizing coils may be activated in order to improve signal-to-noise ratio, as taught in U.S. patent application Ser. No. 12/488,105 by Weinberg, entitled "RADIOMETAL-LABELED AMINO ACID ANALOGS, IMAGING AND THERAPEUTIC AGENTS INCORPORATING THE SAME, AND METHODS USING THE SAME" (incorporated by reference).

In accordance with at least one embodiment, one or more coils or electro-permanent magnets within the MRI system may be fabricated with additive manufacturing, as taught by Urdaneta et al in the 2011 IEEE Medical Imaging Proceedings entitled "Good-bye Wires and Formers: 3-D Additive Manufacturing and Fractal Cooling Applied to Gradient Coils".

The region 110 of desired magnetic profile on one side of the apparatus may not be adjacent to the apparatus, for example it may be one to one hundred centimeters away from the apparatus 100. Magnetic component 210 may be a permanent magnet or may be an electromagnet or may be an electropermanent magnet. Magnetic component 210 may be a discrete magnet or may be a portion of magnetizable material that has been deposited through additive manufacturing and which has been magnetized during or after deposition.

For the purposes of this disclosure an electropermanent magnet may be defined as a combination of hard and soft magnetic material with one or more current-carrying coils, in which the electrical current running through the one or more coils magnetizes the soft magnetic component, as disclosed in U.S. patent application Ser. No. 15/427,426 by Weinberg and Nacev, entitled "METHOD AND APPARATUS FOR MANIPULATING ELECTRO-PERMANENT MAGNETS FOR MAGNETIC RESONANCE IMAGING AND IMAGE GUIDED THERAPY" (incorporated by reference). In this specification, the terms "hard magnetic material" and "soft magnetic material" are used to describe material with varying levels of magnetic coercivity, with the hard magnetic material having a higher magnetic coercivity than the soft magnetic material. It is understood that what we would term "soft magnetic materials" (e.g. Alnico) for purposes of this specification might be considered as "hard magnetic materials" in comparison to some other materials (for example, Permalloy) by certain authorities. Therefore, the terms "hard magnetic material" and "soft magnetic material" are used to illustrate generally many different materials, without specific limitation as to whether the material is universally considered as being "hard" or "soft".

For the purposes of this disclosure, the term "opposing orientation" means an orientation that is not parallel to another orientation. It is understood that the invention can be used in conjunction with other components, for example a generator of radiofrequency electromagnetic fields, to create magnetic resonance images of subjects or structures in a region of interest 110. It is understood that some or all of those subjects or structures may be part or all of a living animal or person or inanimate object. It is understood that interventions such as biopsy or therapy may be carried out in part or wholly using the aperture 120.

It is understood that device 100 may be used in conjunction with other components, for example a computer and/or a power supply and/or coils for generating magnetic and/or electromagnetic fields, in order to attain a desired result of a meaningful image. It is understood that the image may use principles of proton magnetic resonance imaging, or magnetic resonance imaging of other particles (for example electrons or sodium atoms) or other imaging principles (for example magnetic particle imaging, or impedance imaging). It is understood that the apparatus may be used to deliver therapy by manipulating magnetizable materials with the magnetic field produced by the device. It is understood that said manipulation may be performed at one time, and that imaging may be performed at another time, in order to guide said manipulation.

For the purpose of the disclosed embodiments, the term imaging, includes imaging technology that utilize components to form an image using magnetic resonance or magnetic particle imaging. It should be understood that such components include coils or magnets (or electro-permanent magnets) that polarize protons or other nuclei or electrons in one or more structures to be imaged, wherein gradient and/or radiofrequency coils form an image. Thus, although not shown in detail herein, it should be understood that the disclosed embodiments may be used in conjunction with a support structure that may hold an imaging system and may contain other components needed to operate or move the imaging system, for example, wheels and/or batteries.

Moreover, it should be understood that an associated display system is not shown but should be understood to be present in order to view images produced by the imaging system.

Further, it should be understood that disclosed embodiments may image one or more structures for segments of the one or more structure at a time, since it may be difficult in a single-sided MRI to obtain very good uniformity over the entirety of a structure to be imaged. It should be understood that the spatial resolution of certain portions of one or more structures to be imaged, e.g., breast tissues, may be different than in other portions, depending on the gradient applied at the time of image acquisition, which may be useful in order to better characterize certain regions of tissues.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments of, as set forth above, are intended to be illustrative, not limiting. Various changes may be made without departing from the spirit and scope of the invention.

The invention claimed is:

1. An apparatus for imaging one or more structures included in a subject, the apparatus comprising:
one or more arrays of magnetic materials, at least some of the arrays of materials generating magnetic fields in opposition to other materials in the one or more arrays; and
an access aperture provided through the one or more arrays of magnetic materials to provide access for intervention with the subject of the imaging,
wherein a magnetic field is provided on one side of the apparatus for imaging the subject,
wherein the magnetic field on the one side of the apparatus is used to image the subject using magnetic resonance imaging that is at a distance from the apparatus and from the access aperture,
wherein the apparatus is a single sided device for imaging one or more structures and the access aperture extends through the single side.

2. The imaging apparatus of claim 1, wherein the apparatus is used to image a pelvic region of a subject.

3. The imaging apparatus of claim 1, wherein the subject is a living animal or person.

4. The imaging apparatus of claim 1, where the apparatus forms a magnetic resonance imaging system.

5. The imaging apparatus of claim 1, wherein the apparatus is an MRI system which includes electro-permanent magnets.

6. The imaging apparatus of claim 1, wherein an axis of the access aperture is perpendicular to a face of the imaging apparatus.

7. The imaging apparatus of claim 1, wherein the one or more arrays of magnetic materials include at least one magnetizable component that is, at least in part, a hard-magnetic material and at least one magnetizable component that is, at least in part, of a soft-magnetic material.

8. A method of imaging one or more structures that are at least part or a subject, the method comprising:
positioning an array of magnetic materials on one side of the one or more structures, the array forming an imaging apparatus, which is a single sided device having an access aperture for access to the one or more structures; and
imaging the one or more structures using magnetic resonance imaging using the array of magnetic materials positioned on the one side of the one or more structures,
wherein the magnetic field on the one side of the apparatus is used to image the subject that is at a distance from the apparatus and from the access aperture.

9. The imaging method of claim 8, wherein the imaging apparatus is used to image a pelvic region of a subject.

10. The imaging method of claim 8, wherein the subject is a living animal or person.

11. The imaging method of claim 8, where the array forms a magnetic resonance imaging system.

12. The imaging method of claim 11, wherein the MRI system includes electro-permanent magnets.

13. The imaging method of claim 8, wherein an axis of the access aperture is perpendicular to a face of the imaging apparatus.

14. The imaging method of claim 8, wherein the one or more arrays of magnetic materials include at least one magnetizable component that is, at least in part, a hard-magnetic material and at least one magnetizable component that is, at least in part, of a soft-magnetic material.

* * * * *